United States Patent [19]

Van der Knaap

[11] Patent Number: Plant 5,826

[45] Date of Patent: Dec. 9, 1986

[54] KALANCHOE PLANT NAMED ETNA

[75] Inventor: Jacques C. M. Van der Knaap, De Lier, Netherlands

[73] Assignee: Ball Panam Plant Company, Parrish, Fla.

[21] Appl. No.: 706,606

[22] Filed: Feb. 28, 1985

[51] Int. Cl.[4] ..... A01H 5/00

[52] U.S. Cl. ..... Plt./68

[58] Field of Search ..... Plt./68

*Primary Examiner*—R. E. Bagwill

*Attorney, Agent, or Firm*—Schwartz, Jeffery, Schwaab, Mack, Blumenthal & Evans

[57] ABSTRACT

A Kalanchoe plant named Etna, having large orange-red flowers, floriferous habit, medium growth habit, an average 12 weeks crop time, and adaptability for production in pots of varying size.

1 Drawing Figure

1

The present invention relates to a new and distinctive cultivar of Kalanchoe, plant, botanically known as Kalanchoe, and referred to by the cultivar name Etna.

The new cultivar was referred to during the breeding and selection process by the designation Pueblo-×Regulus and is a product of a planned breeding program. The basic objective of the breeding program was to create a new Kalanchoe cultivar having a short crop time, good foliage, good color, and good keeping qualities for a year around Kalanchoe.

The new cultivar was originated by Applicant from a cross made in a controlled breeding program in De Lier, Netherlands. The female, or seed parent was an unpatented cultivar named Pueblo. The male, or pollen parent was a cultivar named Regulus, disclosed in U.S. Plant Pat. No. 4,817.

Etna was discovered and selected by me as a flowering plant within the progeny of the stated cross in a controlled environment in De Lier, Netherlands. Asexual reproduction of the new cultivar by stem cuttings, as performed by me at De Lier, Netherlands, has demonstrated that the combination of characteristics as herein disclosed for the new cultivar are firmly fixed and are retained through successive generations of asexual reproduction.

Etna has not been observed under all possible environmental conditions. The phenotype may vary significantly with variations in environment such as temperature, light intensity and day length. The following observations, measurements and values describe the new cultivar as grown in De Lier, Netherlands, under greenhouse conditions which closely approximate those generally used in commercial practice.

The following traits have been repeatedly observed and are determined to be basic characteristics of Etna, which in combination distinguish this Kalanchoe as a new and distinct cultivar:

1. Excellent orange-red flower color.
2. Medium growth habit compared to other cultivars of this type.
3. Acceptable branch.
4. Suitable for production in 8–12 cm. pots.
5. Floriferous, with large flowers.
6. To reduce peduncle elongation after flower initiation, plants must be treated with Alar or B9.
7. An average 12 weeks crop time.

Etna is most similar to Bali, disclosed in U.S. Plant Pat. No. 5,348. Etna is principally distinguished from

2

Bali by its flower color, keeping qualities, vigor, and shorter crop time.

The accompanying photographic drawing shows a typical specimen plant of the new cultivar. The colors appearing in the photograph are as true as possible with color illustrations of this type.

In the following description, colour references are made to The Royal Horticultural Society Color Chart (R.H.S.), except where general colors of ordinary significance are referred to. Color values are taken under natural light conditions at approximately 12:00 p.m. noon in De Lier, Netherlands.

Botanical classification: Kalanchoe, cv. Etna.

Parentage:

*Male parent.*—Regulus.

*Female parent.*—Pueblo.

Propagation:

(A) *Type cutting.*—Shoot cuttings (B) *Time to root.*—12 days at 21° C. summer, and 17 days winter.

(C) *Rooting habit.*—Many large, thick roots.

Plant description:

(A) *Form.*—Upright, medium-sized. Growing and scheduling practices can produce small plants or large plants.

(B) *Habit of growth.*—Average growth rate for this type of plant. Generally shoots are formed at every node.

(C) *Foliage description.*—Leaves simple, opposite, generally symmetrical. (1) Size: Average, full grown leaf of a flowering plant in a 11 cm. pot is 101 mm. long and 80 mm. wide. (2) Shape: Ovate, apex acute to obtuse, base truncate. (3) Texture: Glabrous, coriaceous, succulent. (4) Margin: Crenate. (5) Color: Young foliage, top side 147A, under side 147C. Mature foliage, top side 147A, under side 147C.

Flowering description:

(A) *Flowering habits.*—Inflorescence of each shoot is formed by dichotomous branching, starting with opening of terminal flower at main axis, followed by terminal flowers of the side branches of the inflorescence. Opening of new buds will continue for seven weeks or more. Individual flowers last two weeks or more after opening.

(B) *Natural flowering season.*—Novenber. Flowering time under controlled day length at 25° C. in summer is 11 weeks; in winter at 20° C., 13 weeks. Flowering time depends on temperature, light intensity and other growing conditions.

(C) *Flower buds.*—Oblong, developing to tubular as petals mature; sheathed with four green sepals; corolla at maturity about 13 mm. (1) Size: 14 mm. (2) Shape: Oblong. (3) Rate of Opening: Normal.

(D) *Flowers borne.*—Compound dichasial cyme on strong peduncles. Peduncle length up to 5 mm., depending on growing conditions and applications of B9 or Alar.

(E) *Quantity of flowers.*—Very floriferous, with new buds continuing to develop.

(F) *Petals.*—(1) Shape: Nearly round, apex cuspidate. (2) Color: Top side when opening, 33A, fading to 34A; under side, 35D. (3) Number and size of petals: Four, united in corolla; petals, 7 mm. in diameter, total diameter.

(G) *Reproductive organs.*—(1) Stamens: Eight in number. (a) Anther shape: Flat, elliptical. (b) Filament color: Yellow. (c) Pollen color: Yellow. (2) Pistels (a) Stigma shape: Flat, crystalline. (b) Style color: Greenish-white. (c) Ovaries: Four-celled, 7 mm. long, green.

Disease resistance: No known Kalanchoe diseases observed to date.

I claim:

1. A new and distinct cultivar of Kalanchoe named Etna, as described and illustrated, and particularly characterized by its large orange-red flowers, floriferous habit, medium growth habit, an average 12 weeks crop time, and by its adaptability to pots of varying size.

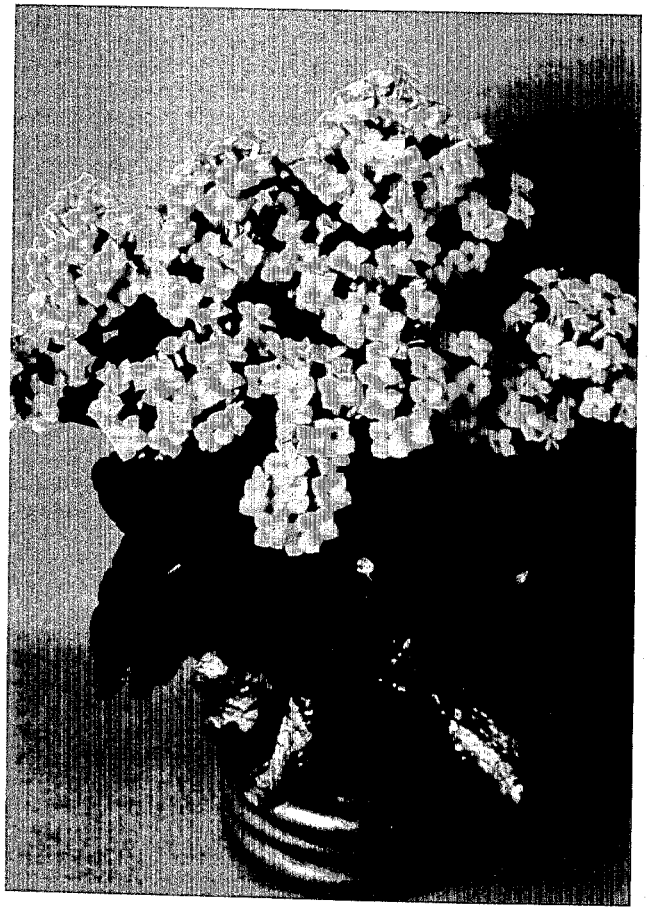

* * * * *